Nov. 22, 1960 F. C. RAFFEL Plant Pat. 1,987
ROSE PLANT
Filed Feb. 8, 1960
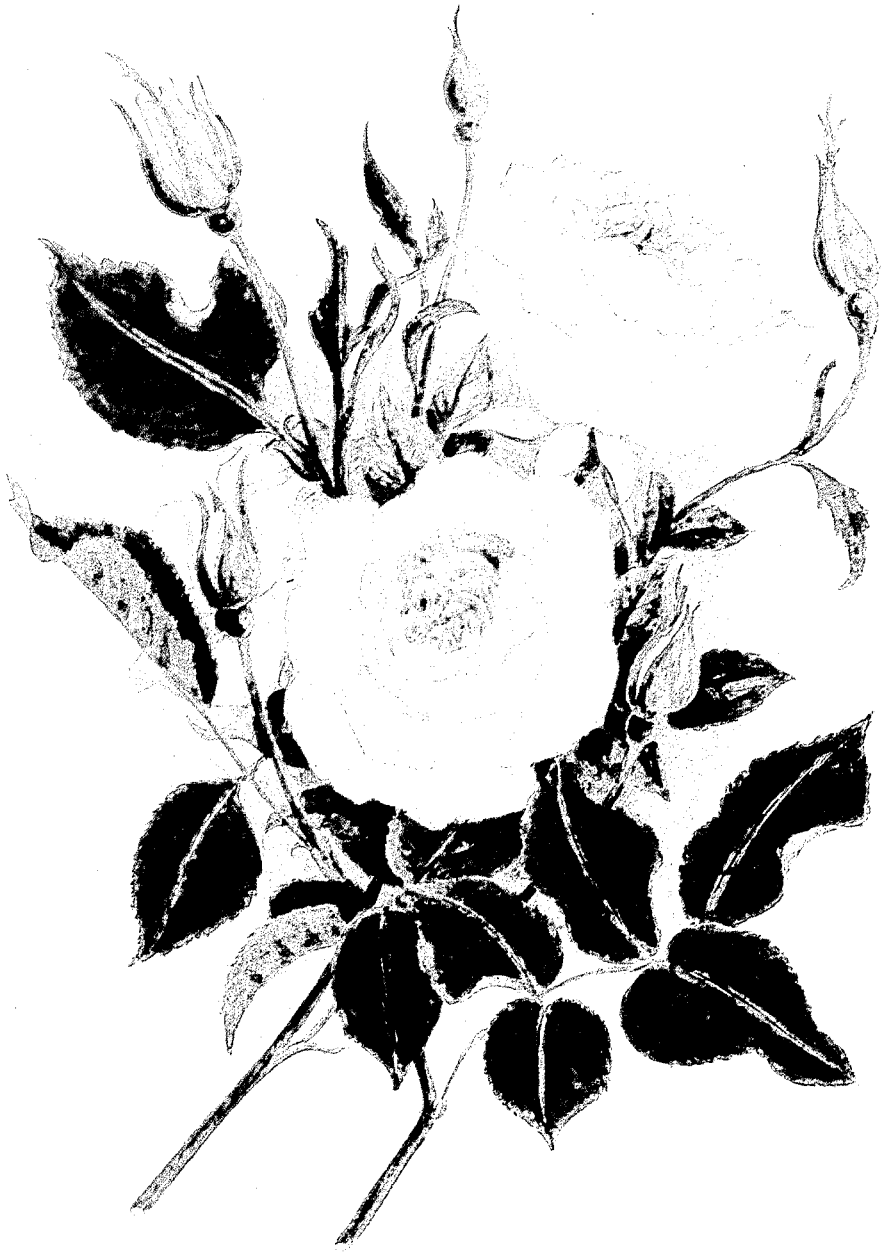
WITNESS
Addison E Avery
INVENTOR
Frank C. Raffel
Webster & Webster
ATTYS.

United States Patent Office

Plant Pat. 1,987
Patented Nov. 22, 1960

1,987

ROSE PLANT

Frank C. Raffel, 2910 E. Main St., Stockton, Calif.

Filed Feb. 8, 1960, Ser. No. 7,499

1 Claim. (Cl. 47—61)

This invention relates to a new and distinct variety of rose plant, of half-hardy, tall, bush type, and of the florabunda class.

The variety is characterized, in comparison to its parentage hereinafter described, by a vigorous bush which is better shaped, with less thorns; by more and larger leaflets closer to the flowers; by highly attractive double petalage flowers which in the bud stage and when the calyx first breaks are red, but upon opening are a brilliant white with the petals margined, and blotched adjacent the margin, in red, with a slight shading to yellow at the base; and by flowers which persist in color and keep in good condition longer after opening. The color of the flowers is the predominant feature of novelty.

I originated the present variety, in my experimental nursery located near Stockton, San Joaquin County, California, as a cross between Little Darling (United States Plant Patent No. 1,581) as the seed parent and Gertrude Raffel (unpatented) as the pollen parent. After I originated the variety as above, and upon recognition of its novel characteristics, it was asexually reproduced by me, in my experimental nursery located as aforesaid, by budding from the original seedling; the asexual reproductions having run true in all respects.

The figure of the drawing illustrates a spray, including foliage, buds, and flowers.

Referring now specifically to the new and distinct variety of bush-type rose plant, the following is a detailed description thereof in outline; all major color plate identifications being by reference to Maerz and Paul Dictionary of Color, except where common terms of color definition are employed.

Type: Half-hardy; tall; bush.
Class: Florabunda.
Flowers:
*Continuity.*—Continuous during growing season.
*Fragrance.*—Slight.
Flowers borne: Five or more to stem, in irregular cluster on normal stems.
Quantity of bloom: Abundant outdoors.
Bud:
*Peduncle.*—Short; medium; almost smooth; few brown hairs. Color—medium bronze.
*Before calyx breaks.*—Size—small. Form—short; pointed, with a conspicuous neck; foliaceous appendages on the surface of the bud, with slender foliaceous parts extending beyond the tip equal to three quarters or more of its length.
*As calyx breaks.*—Color—red.
*As first petal opens.*—Size—small. Form—medium length; pointed. Color—outside—red; inside—white, margined in red, with yellow at base.
Bloom:
*Size.*—Small (but medium for a florabunda). When fully open average 2½" to 3½".

*Petalage.*—Double—but stamens not hidden. Average 18 to 28 petals arranged regularly.
*Form.*—Cupped at first, becoming flat. Petals at first very tightly rolled outward. Petals at maturity tightly rolled outward.
Petals: Thick; inside velvety; outside satiny.
*Shape.*—Obovate, with outside petals having one to two notches. Usually one point to petal.
*Color.*—Outside surface of petals—white (1–A–1) margined, and blotched adjacent the margin in red (3–A–4 to 3–A–5), with light yellow (9–D–1) at the base. Inside surface of petals—White (1–A–1), margined, and blotched adjacent the margin, in red (1–A–3 to 1–A–4), shading deeper red (1–G–6) at the center of the flower, with light yellow (9–J–1) at the base. The inner petals tend to have a wider margin of red. Outdoors and in direct strong sunshine for three or four days, the petals frequently turn to substantially all red.
*Behavior.*—Persist.
*Flower longevity.*—Bush in garden—ten days in moderate weather. Cut roses grown outdoors, kept at living room temperature—eight days.
Reproductive organs:
*Stamens.*—Medium number; regularly arranged.
*Filaments.*—Medium length; white to light yellow.
*Anthers.*—Medium size; yellow.
*Pollen.*—Moderate yellow.
*Pistils.*—Medium number
*Styles.*—Uneven; medium length; medium thickness; bunched.
*Stigma.*—White to light yellow.
*Ovaries.*—All enclosed in calyx.
*Hips.*—Pear shaped; gray-green to yellow; moderately smooth; walls thin.
*Sepals.*—Moderate length; spear shaped; recurved; medium green on outside, gray-green on inside.
*Seeds.*—Few; small.

*Plant*

Foliage:
*Leaves.*—Compound of three to seven leaflets; abundant; medium size; heavy, glossy.
*Leaflets.*—Shape—widely variant. Color—young leaves: upper surface—bronze; under surface—bronze; mature leaves: upper surface—dark green (24–L–12); under surface—lighter green (22–I–5). Rachis—medium strength; upper side—grooved; under side—smooth; seldom any prickles or thorns. Stipules—medium length, with medium length points turning out at all angles, some less than 45 degrees and some curved toward the stem.
Growth:
*Habit.*—Bushy; upright; much branched.
*Growth.*—Vigorous.
*Canes.*—Medium strength.
*Main stems.*—color—bronze. Thorns—few; medium length; hooked downward, with long narrow base. Prickles—few; brown. Hairs—few; bronze.
*Branches.*—Color—bronze. Thorns—few; variant sizes, but mostly small; hooked downward, with long narrow base. Prickles—few; reddish. Hairs—few; reddish.
*New shoots.*—color—bronze. Thorns—few; medium length; hooked downward, with long narrow base. Prickles—few; reddish. Hairs—few; reddish.

The rose plant and its flowers as herein described may vary in slight detail due to climatic and soil conditions under which the variety may be grown; the present description being of the variety as grown near Stockton, San Joaquin County, California.

The following is claimed:

A new and distinct variety of half-hardy, tall, bush-type rose plant of the florabunda class—as illustrated and described—characterized, in comparison to the seed parent Little Darling and the pollen parent Gertrude Raffel, by a vigorous upright bush which is better shaped with less thorns; by abundant dark green foliage having more and larger leaflets closer to the flowers; by highly attractive double petalage flowers which in the bud stage and when the calyx first breaks are red and upon opening are a brilliant white with the petals margined, and blotched adjacent the margin, in red, with light yellow adjacent the base; and by flowers which persist in color and keep longer after opening.

No references cited.